United States Patent
Badger et al.

(10) Patent No.: US 7,974,802 B2
(45) Date of Patent: Jul. 5, 2011

(54) PHOTOMASK IMAGE INSPECTION

(75) Inventors: Karen D. Badger, Milton, VT (US); Jim B. Densmore, Morrisville, VT (US); Christopher R. Gillman, Burlington, VT (US); Kathleen G. Purdy, Richmond, VT (US); Cynthia Whiteside, Charlotte, VT (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 12/044,032

(22) Filed: Mar. 7, 2008

(65) Prior Publication Data

US 2009/0228228 A1    Sep. 10, 2009

(51) Int. Cl.
*G01N 37/00* (2006.01)

(52) U.S. Cl. .............. 702/83; 702/35; 702/82; 382/144; 382/149; 430/5; 700/109; 700/117

(58) Field of Classification Search .................... 702/82, 702/83, 35; 382/213, 144, 149; 438/16, 438/4, 949; 716/19, 21; 703/13; 430/5, 430/22; 700/109, 117
See application file for complete search history.

(56) References Cited

U.S. PATENT DOCUMENTS

| 6,526,164 | B1 | 2/2003 | Mansfield et al. | |
| 6,922,600 | B1* | 7/2005 | Conrad et al. | 700/108 |
| 7,257,247 | B2 | 8/2007 | Bruce et al. | |
| 7,340,352 | B2* | 3/2008 | Takahashi et al. | 702/35 |
| 2004/0191649 | A1* | 9/2004 | Dao et al. | 430/5 |
| 2005/0033467 | A1* | 2/2005 | Purdy | 700/109 |
| 2005/0246049 | A1* | 11/2005 | Suttile et al. | 700/117 |
| 2006/0195215 | A1* | 8/2006 | Suzuki et al. | 700/109 |
| 2006/0235560 | A1* | 10/2006 | Ogawa et al. | 700/109 |
| 2007/0162242 | A1* | 7/2007 | Singh et al. | 702/82 |

* cited by examiner

*Primary Examiner* — Carol S Tsai

(74) *Attorney, Agent, or Firm* — Gibb I.P. Law Firm, LLC; Richard M. Kotulak, Esq.

(57) ABSTRACT

A method optimizes photomask inspection. After masks are manufactured, the method predicts the likelihood that the masks will be defect free based on defect criteria, etch area, etch mode, and etch tool type associated with the masks. The method skips an initial mask inspection for masks that have a predictability value above a predetermined value and performs the initial mask inspection for masks that have a predictability value below the predetermined value. After initial inspection is preformed (or skipped), a pellicle is mounted on the mask and then all masks are inspected or reinspected for defects and foreign matter.

15 Claims, 1 Drawing Sheet

PHOTOMASK IMAGE INSPECTION

BACKGROUND

1. Field of the Invention

The embodiments of the invention generally relate to a method of optimizing photomask inspection that skips initial mask inspection based on etch mode, tool type, defect criteria, and etch area.

2. Description of Related Art

Semiconductor photomask manufacturing requires that all masks be defect and foreign material (FM) free for use in the semiconductor fabricator. Because a photomask pattern is repeated many times across a wafer, a defect on a mask can affect the image printed, resulting in wafer yield loss. In extreme cases, defects of this nature can produce a zero yield wafer. In photomask manufacturing, a mask is typically inspected for defects and foreign material two or more times during the process. If a defect occurs on a mask and the mask is inspected early in the process, defects can be repaired, or a new mask can be started early enough to meet customer serviceability requirements. While mask inspection is one of the most important steps in photo mask manufacturing, it is also one of the most time consuming and expensive processing steps. In order to manage cost and remain competitive in the marketplace there is a need to reduce the number of times a mask is inspected while still meeting serviceability requirements.

Mask inspection tools represent some the most complex systems used in the semiconductor industry, on par in cost and complexity with lithography expose tools and mask pattern generators. The complexity of mask inspection tools is driven by the need for high resolution and high speed in detection of defects. The first or initial inspection generally occurs after front end processing and prior to pellicle mount. This inspection checks for defects that occur during the print, develop and etch process. A final inspection occurs after a pellicle is mounted to assure no defects or foreign material were added during the pellicle mounting process. The initial inspection is done at a point where most of the processing of the mask has been completed and most defects would have been introduced. It is also done at a point where, if defects are found, they can be repaired, or another mask can be started and completed in order to meet manufacturing commitments or serviceability to the semiconductor fabricator. If, however, one can predict which masks are likely to be defect free after front end processing, one may skip the first inspection, saving significant time and money.

Inspection strategies exist today that allow initial inspection to be skipped based on defect size specifications and inspection tool availability. Defect size specification or defect criteria is the maximum size defect allowable on a mask in that it has no affect on the image printed on the wafer. Based on the current strategy, masks with large defect criteria may skip initial inspection if there is no inspection tool available when front end processing is complete. Because this current 'skip' inspection strategy is based only on defect criteria and available inspection tool capacity, it can miss many defects, resulting in pellicle demount for repair in many cases.

SUMMARY

An embodiment herein comprises a method of optimizing photomask inspection. With the method, after masks are manufactured, the method predicts the likelihood that the masks will be defect free based on the defect criteria, the etch area, the etch mode, and the etch tool type that are associated with the masks (in some embodiments these are the only factors that are considered). The defect criteria and the etch area are measured in any conventional units, in one of multiple dimensions. The etch mode comprises either a wet mode or a dry mode.

For masks that have a predictability value that is high enough (e.g., above some predetermined value), the initial mask inspection can be skipped. To the contrary, the initial mask inspection is performed for masks that have too low of a predictability value (e.g., below some predetermined value). After the initial inspection is performed or skipped, a pellicle is mounted on each mask and a second mask inspection is performed.

These and other aspects of the embodiments of the invention will be better appreciated and understood when considered in conjunction with the following description and the accompanying drawing. It should be understood, however, that the following descriptions, while indicating embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which.

DETAILED DESCRIPTION OF EMBODIMENTS

Figure 1:
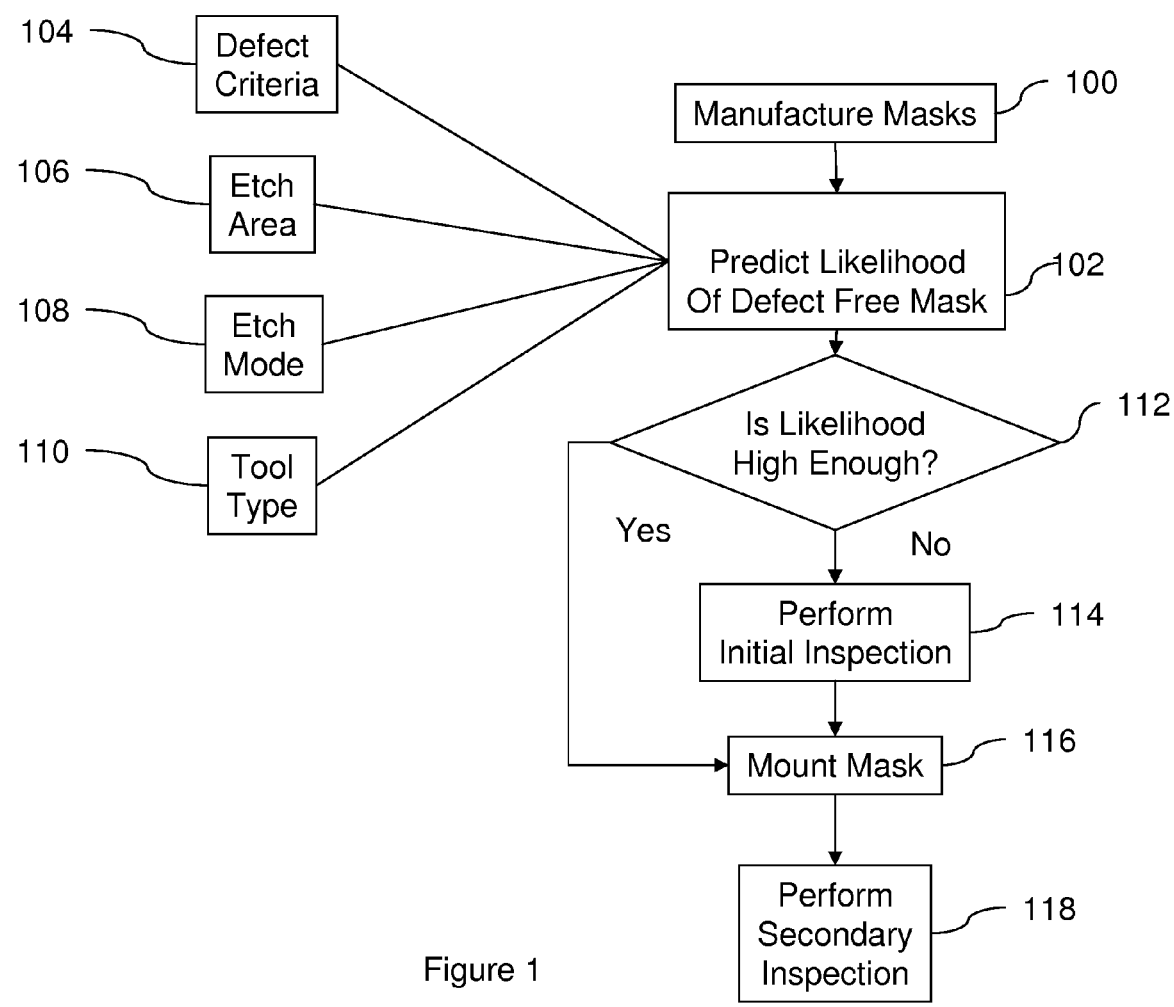
FIG. 1 is a flow diagram illustrating a method embodiment of the invention.

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

Presented here is a method to predict which categories of photomasks are likely to be free of defects and foreign material after front end processing based on factors that actually contribute to defect density. Because the embodiments herein use causal effects, they are a much better predictor of which masks may be appropriately selected to skip initial inspection compared to the current processes. The embodiments herein accomplish this through the use of defect criteria, etch area, etch mode and etch tool to predict the probability of a mask being defect and foreign material free.

Since some masks have a lower probability of being defect and foreign material free, these masks can then be prioritized at the inspection tools to receive early initial inspections as well as a final inspection. Others with a high probability of being defect and foreign material free can skip initial inspection saving valuable time and money.

As shown in flowchart form in FIG. 1, an embodiment herein comprises a method of optimizing photomask inspection. After masks are manufactured in item 100, the method predicts the likelihood that the masks will be defect free in item 102 based on the defect criteria 104, the etch area 106, the etch mode 108, and the etch tool type 110 that are associated with the masks. In some embodiments these are the only factors that are considered in predicting the likelihood that the masks will be defect free.

The defect criteria 104, the etch area 106, the etch mode 108, and the etch tool type 110 can be input as part of the mask specifications. The defect criteria 104 and the etch area 106 are measured in any conventional units, in one or multiple dimensions (e.g., um, um$^2$, etc.). The etch mode 108 used to make the mask comprises either a wet mode or a dry mode, and the etch tool type 110 which was used to etch the mask can refer to whether the tool is a combination tool (two or more joined tools) or a stand-alone tool (single tool), the tool manufacturer, the tool model, etc.

The prediction made in item 102 can weight each of the above factors equally, or can assign greater weight to some factors relative to other factors. In addition, the prediction can be made by generating various size limits (for defect size and etch area) that could be different depending upon what type of etch mode or tool type would be involved.

These predictions are based on historical results and can be changed as historical results change over time. For example, it may be found that, for a given etch mode or tool type, 85% of masks with etch area of less than 500 mm$^2$ and 80% of masks with etch area of less than 1500 mm$^2$ had no defects. Similarly, it could have been found historically that 66% of masks with a given defect criteria (e.g., greater than or equal to 0.5 um) may have had no defects. It could have also been found historically that the percentage of defect free masks does not change as the defect criteria changes (e.g., between 0.5 and 1.3 um). 92% of masks with a defect criteria greater than 0.5 um processed on a dry etch tool could be defect free, while only 87% of masks with a defect criteria greater than 0.5 um processed on a wet etch tool could be defect free. These and other similar historical results could be used to make predictions regarding whether a mask would be defect free.

Referring back to FIG. 1, as determined by decision box 112, for masks that have a predictability value (e.g., a percentage in the examples shown above) that is high enough (e.g., in situations where the percentage likelihood that the mask is defect free is above some predetermined value (where a "predetermined value" is some number, or percentage that has been determined previously), the initial mask inspection process 114 can be skipped. To the contrary, the initial mask inspection 114 is performed for masks that have too low of a predictability value (e.g., in situations where the percentage likelihood that the mask is defect free is below some predetermined value, which can be the same or different that the previous predetermined value). For various inspection techniques, see U.S. Pat. Nos. 7,257,247, 6,526,164, the complete disclosure of which is incorporated herein by reference.

After the initial inspection 114 is performed or skipped as determined by decision box 112, the masks are mounted with Pellicle mounts 116 and a second mask inspection 118 is performed on all of the masks after mounting the masks with the mounts.

Because the embodiments herein utilize causal effects, they are much better predictor of which masks may be appropriately selected to skip initial inspection compared to the current processes. The embodiments herein reduce the percentage of skipped masks with defects at first as compared to some current methods.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of embodiments, those skilled in the art will recognize that the embodiments of the invention can be practiced with modification within the spirit and scope of the appended claims.

What is claimed is:

1. A method of optimizing photomask inspection, said method comprising:
    manufacturing masks;
    predicting a likelihood, using percentages, that said masks will be defect free based on defect criteria, etch area, etch mode, and etch tool type associated with said masks, wherein said etch mode comprises one of a wet mode and a dry mode, and wherein said predicting further comprises weighting factors considered in said predicting;
    skipping an initial mask inspection for masks that have a defect-free probability percentage above a value; and
    performing said initial mask inspection for masks that have a defect-free probability percentage below said value;
    mounting said masks with pellicles; and
    performing a second mask inspection on all of said masks after mounting said masks in said pellicles.

2. The method according to claim 1, said initial mask inspection and said second mask inspection checking for foreign matter on said masks.

3. The method according to claim 1, said initial mask inspection and said second mask inspection checking for mask defects.

4. The method according to claim 1, said defect criteria comprising defect size limits.

5. The method according to claim 1, said etch tool type comprising whether a tool is a combination tool or a stand-alone tool, a tool manufacturer, and a tool model.

6. A method of optimizing photomask inspection, said method comprising:
    manufacturing masks;
    predicting a likelihood, using percentages, that said masks will be defect free based only on defect criteria, etch area, etch mode, and etch tool type associated with said masks, wherein said etch mode comprises one of a wet mode and a dry mode, and wherein said predicting further comprises weighting factors considered in said predicting;
    skipping an initial mask inspection for masks that have a defect-free probability percentage above a value; and
    performing said initial mask inspection for masks that have a defect-free probability percentage below said value;
    mounting said masks with pellicles; and
    performing a second mask inspection on all of said masks after mounting said masks in said pellicles.

7. The method according to claim 6, said initial mask inspection and said second mask inspection checking for foreign matter on said masks.

8. The method according to claim 6, said initial mask inspection and said second mask inspection checking for mask defects.

9. The method according to claim 6, said defect criteria comprising defect size limits.

10. The method according to claim 6, said etch tool type comprising whether a tool is a combination tool or a stand-alone tool, a tool manufacturer, and a tool model.

11. A method of optimizing photomask inspection, said method comprising:
   manufacturing masks;
   predicting a likelihood, using percentages, that said masks will be defect free based on defect criteria, etch area, etch mode, and etch tool type associated with said masks;
   skipping an initial mask inspection for masks that have a defect-free probability percentage above a value; and
   performing said initial mask inspection for masks that have a defect-free probability percentage below said value;
   mounting said masks with pellicles; and
   performing a second mask inspection on all of said masks after mounting said masks in said pellicles.

12. The method according to claim 11, said initial mask inspection and said second mask inspection checking for foreign matter on said masks.

13. The method according to claim 11, said initial mask inspection and said second mask inspection checking for mask defects.

14. The method according to claim 11, said defect criteria comprising defect size limits.

15. The method according to claim 11, said etch tool type comprising whether a tool is a combination tool or a stand-alone tool, a tool manufacturer, and a tool model.

* * * * *